United States Patent [19]

Lämsä et al.

[11] Patent Number: 5,747,434
[45] Date of Patent: May 5, 1998

[54] ENZYMATIC PROCESS FOR PREPARING A SYNTHETIC ESTER FROM A VEGETABLE OIL

[75] Inventors: Merja Lämsä, Merimasku; Yu-Yen Linko; Pekka Linko, both of Espoo; Esa Uosukainen, Helsinki, all of Finland

[73] Assignee: Raisio Yhtyma Oyj, Raisio, Finland

[21] Appl. No.: 793,991

[22] PCT Filed: Sep. 7, 1995

[86] PCT No.: PCT/FI95/00478

§ 371 Date: Mar. 4, 1997

§ 102(e) Date: Mar. 4, 1997

[87] PCT Pub. No.: WO96/07751

PCT Pub. Date: Mar. 14, 1996

[30] Foreign Application Priority Data

Sep. 7, 1994 [FI] Finland ................................. 944119

[51] Int. Cl.$^6$ ................................................. C10M 141/02
[52] U.S. Cl. .............................................. 508/485; 508/491
[58] Field of Search ........................... 508/491, 485; 435/135

[56] References Cited

U.S. PATENT DOCUMENTS

| | | | |
|---|---|---|---|
| 4,420,560 | 12/1983 | Matsuo et al. | 435/134 |
| 4,451,564 | 5/1984 | Struve et al. | 435/55 |
| 4,874,699 | 10/1989 | Maruzeni et al. | 435/135 |
| 5,338,471 | 8/1994 | Lal | 508/491 |

OTHER PUBLICATIONS

Patent Abstract of Japan, vol. 12, No. 191, C–501, Abstract of JP, A, 62–296884 (Chiyoda Chem. Eng. & Constr. Co. Ltd.), 24 Dec. 1987.

*Primary Examiner*—Margaret Medley
*Attorney, Agent, or Firm*—Pollock, Vande Sande & Priddy

[57] ABSTRACT

A two step process for preparing a synthetic ester from a vegetable oil by means of lipase enzymes. A lubricant composition comprising a synthetic ester prepare by said process.

20 Claims, No Drawings

ENZYMATIC PROCESS FOR PREPARING A SYNTHETIC ESTER FROM A VEGETABLE OIL

The objects of the present invention are a process for preparing a synthetic ester from a vegetable oil by means of lipase enzymes, and lubricants which contain a synthetic ester prepared by said process.

Natural fats and oils have been used as lubricants already for thousands of years. With industrialization mineral based lubricants came also to the market. The applications of lubricants and thus also the requirements set for them have changed and developed with the advance of technology. Various types of synthetic esters and lubricants containing the same have been developed to meet the new requirements.

The purpose of a lubricant is to minimize friction and wear of metals. Lubricants are developed according to the use and they consist of a base fluid and additives improving the lubricative properties. With the development of technology, lubricants are used under more and more severe conditions, such as at very low or very high temperatures (e.g. the turbine engines of aeroplanes). At the same time biodegradability, non-accumulation to the environment, non-toxicity and the use of renewable raw materials have emerged as new requirements. The use of biodegradable lubricants is of particular importance in the machines and devices used in the fields of agriculture, forestry and building, as the oil used may be left in the environment.

By the synthetic esters developed as lubricants are meant esters prepared from mono-, di- or trialcohols and mono- or dicarboxylic acids by known esterification and transesterification methods. The conventional chemical process comprises combining all the reactants and letting them react in one stage. The reaction may be carried out in the presence of catalysts, such as acids, bases or metal oxides. In addition to chemical agents, also lipase enzymes can act as catalysts of transesterification reactions.

Lipases (triacylglycerol acylhydrolase; EC 3.1.1.3) belong to the esterase enzyme group, and fats and oils are their natural substrates. Several microbes (yeasts, molds, bacteria) secrete in their growth media lipases by means of which lipids decompose into nutrients of the microbe. Lipases catalyze the hydrolysis reactions of oils and fats but under suitable conditions they also catalyze the synthesis and transesterification of tri-, di- and monoglyceride esters (Yamane et al., J. Am. Oil Chem. Soc. 64, 1987, 1657–1662).

On the basis of their specificity, lipases are divided into three groups, nonspecific, 1,3-specific and fatty acid specific lipases. Nonspecific lipases are produced by for instance the yeast *Candida rugosa* (ex. *cylindracae*) and the bacteria *Corynebacterium acnes* and *Staphylococcus aureus*. Nonspecific lipases release fatty acids from all three positions of a triglyceride. According to their name, 1,3-lipases release fatty acids from positions 1 and 3 of triglycerides. These lipases are produced by for instance the molds *Aspergillus niger*, *Mucor javanicus*, *Mucor miehei* and *Rhizopus arrhizus* as well as by the yeast *Candida lipolytica*. The fatty acid specific lipases release only certain fatty acids from triglycerides. *Mucor miehei*, for example, produces also a lipase which in addition to 1,3-specificity is also specific to fatty acids with 12 carbon atoms. However, the specificity is not absolute.

The structure of the synthetic ester used has a profound effect on the stability of the lubricant. Esters decompose by the effect of heat and/or oxygen. It is known to increase the thermal stability of synthetic esters by using in the preparation no beta hydrogen alcohols. Oxidative properties on the other hand can be improved by deuteration of esters.

Synthetic esters intended for a lubricative use are classified by structure as monocarboxylic acid, dicarboxylic acid, polyol and complex esters. Due to their low viscosity and high volatility monoesters are poorly suitable as lubricants. Polyol esters are chemically more stable than for example diesters, due to the structure of the polyols used in the preparation of said esters wherein no hydrogen atom is attached to the β carbon atom. Complex esters have promising lubricative properties but the manufacture thereof on an industrial scale is difficult because of the severe conditions required by the reaction, especially if said esters are prepared from (purified) fatty acids and alcohols.

If polyol esters are prepared by using no alfa hydrogen acids, the stability properties of the esters can be further improved. Metro et al. (CA 859 771) have shown that the no alfa hydrogen carboxylic acids increase the thermal and oxidative stability of esters prepared from no beta hydrogen alcohols, as well as slow down the hydrolysis of the esters.

As the low viscosity polyol esters are not suitable for traditional uses wherein high viscosity is required, it has been aimed at preparing polyol esters of higher viscosity from for example trimethylol propane (TMP). However, it has been found that it is difficult to obtain simple TMP esters with both high viscosity and a low pour point (cf. for example U.S. Pat. No. 4,061,581).

Products based on vegetable oils are nowadays used more and more as lubricants because of their safety to the environment. Natural vegetable and animal oils are glyceride diesters, i.e. tri-, di- or monoesters of glycerol and straight chain saturated and unsaturated fatty acids. The lubricant industry uses for instance rapeseed, rape, soybean, castor, olive, coconut, palm and tall oils.

The advantageous properties of vegetable oils include user friendliness and non-toxicity. In addition, vegetable oils are renewable raw materials and degrade in the environment without accumulating in the food chain of nature. However, the use of vegetable oils as lubricants has been limited by their poor stability properties. The poor thermal and oxidative stability is due to unsaturated and polyunsaturated fatty acids. On the other hand, the unsatisfactory behaviour of vegetable oils at low temperatures is due to the saturated fraction of fatty acids. By using suitable additives and by favouring in cultivation such varieties which do not have a too high degree of saturation, it has been possible to somewhat improve the stability properties. Also the purification of the oil for technical use is helpful.

Furthermore, attempts have been made to modify natural glyceride esters in order to improve their stability properties. Known processes include catalytic hydrogenation, alcoholysis, geometrical isomerization and sulfurization. For example by hydrogenation a certain amount of double bonds from the unsaturated part of vegetable oils can be removed, and by isomerization the amount of undesired isomers can be decreased.

Van der Waal and Kenbeek have presented a process for the preparation of synthetic esters from vegetable oils or animal fats (Proceedings of the Tribology 2000, 8th International Colloqium, Technische Akademie Esslingen, Germany, 14–16 June 1992, Vol II, pp 13.3-1–13.3-8). The process comprises first decomposing the glyceride esters of the starting material into fatty acids and glycerol and subsequently separating the fatty acid fraction into liquid and solid phases. The fatty acids of the liquid phase are separated by distillation into single fatty acids which can be further modified e.g. by hydrogenation or cracking to obtain the desired raw material. Fractions containing a single fatty acid are esterified with no beta hydrogen polyols for preparing a synthetic ester.

The fatty acids of the ester prepared according to the above described process usually contain less unsaturated double bonds than the fatty acids of the starting material, which improves the oxidative stability. However, the costs of the process are extremely high, due to the multistage separation and purification reactions and the most severe conditions (high pressure and temperature) required by the reaction. Moreover, it has been found that when fractions containing only a single fatty acid are reacted with polyols, plenty of mono- and diglycerides are formed, i.e. all the OH groups of the polyols do not react. This decreases the triglyceride yield and the raw material has to be recycled several times if the yield is to be improved. Furthermore, the reaction of a fatty acid and an alcohol creates water which has to be removed during the reaction.

Transesterification of fats by means of lipases is known as such. The literature in the field discloses especially various systems for the immobilization of the lipases used (cf. for example EP patent application 579 928 and U.S. Pat. Nos. 4,798,793 and 4,818,695). The immobilization of lipases facilitates their application both in continuous and batch processes. Patent publication GB 1 577 933 discloses a process for modifying triglycerides with a lipase, especially with an immobilized lipase. However, the literature in the art does not describe the use of lipases as a catalyst in the process according to the present invention.

According to the invention it has now been found that it is possible to prepare synthetic esters with good lubricative properties from vegetable oils by an enzymatic process which avoids the multistage reaction with several separations and recyclings and by which good yields are obtained.

In the process according to the invention a vegetable oil is first transesterified by reacting the vegetable oil with a lower alkanol to obtain a mixture of fatty acid lower alkyl esters. The process is characterised in that the mixture of esters obtained from the first reaction is further transesterified by reacting said mixture with a no beta hydrogen polyol of the formula

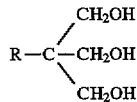

wherein R is a $C_1$–$C_6$ alkyl group, particularly a $C_1$–$C_4$ alkyl group, or a —$CH_2OH$ group, in the presence of a lipase enzyme, and the synthetic ester obtained is recovered.

Vegetable oils suitable as a starting material in the process are for example rapeseed, rape, soybean, castor, olive, coconut, palm, tall, maize, walnut, flaxseed, cotton, sunflower, sesame and almond oils, especially rapeseed oil, rape oil, tall oil and soybean oil, particularly rapeseed oil or rape oil.

The first transesterification reaction of the process according to the invention is carried out by a process known per se, by reacting a refined or alkalirefined vegetable oil with a lower alkanol to obtain a mixture of fatty acid lower alkyl esters.

The lower alkanol used in the first transesterification reaction is preferably a $C_1$–$C_4$ alkanol, especially methanol or ethanol. The obtained mixture of lower alkyl esters of the vegetable oil is thus preferably a mixture of $C_1$–$C_4$ alkyl esters, especially a mixture of methyl or ethyl esters. If desired, usual esterification catalysts may be used in the reaction, and the amounts of the reactants and the reaction conditions (pressure, temperature, reaction time) are either commonly known or easily chosen by a person skilled in the art. The reaction may also be carried out by using a suitable enzyme as a catalyst.

The first transesterification reaction may be illustrated by the following general reaction scheme I:

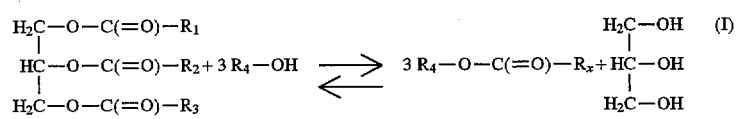

wherein $R_1$, $R_2$ and $R_3$ are fatty acid residues, $R_4$ is an alkyl residue, especially a $C_1$–$C_4$ alkyl residue, and $R_x$ is $R_1$, $R_2$ or $R_3$. Glycerol is formed as a by-product.

The fatty acid lower alkyl ester obtained from the first transesterification reaction is thus a mixture comprising various fatty acids of the vegetable oil used as the starting material. It is typical of the invention that this mixture of fatty acid lower alkyl esters may be used directly as the starting material of the second transesterification reaction without separation or purification of fatty acids.

In the second transesterification reaction according to the invention, the mixture of fatty acid lower alkyl esters obtained from the first transesterification reaction is reacted with a no beta hydrogen polyol, such as for example trimethylol ethane, trimethylol propane, trimethylol butane or pentaerythritol, especially with pentaerythritol or trimethylol propane, in the presence of a lipase.

The second transesterification reaction may be illustrated with the following general reaction scheme II:

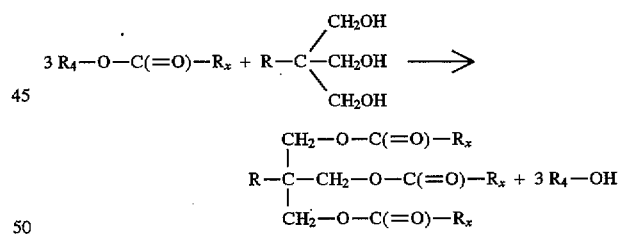

wherein $R_4$ and $R_x$ have the same meanings as in the reaction scheme I and R is a $C_1$–$C_6$ alkyl group, especially a $C_1$–$C_4$ alkyl group, or a —$CH_2OH$ group.

Consequently, it is the question of a totally different chemical reaction than in the process of the prior art wherein a free fatty acid is esterified with an alcohol. In the process according to the invention, an ester is reacted with an alcohol, and thus it is the question of a transesterification reaction which reaction, as well as the reaction conditions required by it and the by-products formed therein, is totally different from the reaction used in the process of the prior art.

The synthetic ester obtained from the second transesterification reaction is recovered and, if desired, purified by conventional methods, for example by neutralization and washing with an aqueous acid. No distillation or any other special treatment is needed as the obtained ester is ready to use as such as a raw material of lubricants.

When a polyol is reacted with a mixture of fatty acid lower alkyl esters in the presence of a suitable lipase, almost all OH-groups of the polyol react into triglycerides. From 75 to 98% of the theoretical yield of the triglyceride is obtained, the proportion of mono- and diglycerides being in total from about 2 to 25%. The product obtained does not contain any free fatty acids which makes it an especially advantageous raw material for lubricants wherein the oxygenation of free fatty acids would cause problems (corrosion, change of viscosity). The process is well adapted for industrial scale and the synthetic ester obtained has better stability properties than the vegetable oil used as the raw material, while at the same time the advantageous properties of a vegetable oil (biodegradability, non-toxicity, user friendliness) are maintained.

By the process according to the invention it is thus possible to prepare synthetic esters from vegetable oils, for example from rapeseed oil, in a yield of even over 95% of the theoretical. In this case, the di- and monoglycerides of the product are also calculated in the yield. During the tests carried out it has been observed that the advantageous properties of the product are maintained in spite of the moderate (up to 30%) di- and monoglyceride content.

The no beta hydrogen polyol and the mixture of esters are preferably reacted with each other in a molar ratio of about 1:2 to 1:6, especially in the molar ratio of about 1:3 to 1:3,5.

The second transesterification reaction, being characteristic of the invention, is preferably carried out in a reduced pressure generator provided with reflux, for example under negative pressure of 2.0 to 12 MPa, preferably under negative pressure of 5.3 MPa. The reaction is carried out at a temperature wherein the lipase used is active, for example at a temperature between 37° C. and 69° C., preferably at a temperature between 42° C. and 47° C. A suitable reaction time is from 24 hours up to 72 hours, depending on the other conditions and the enzyme used. It is preferred to add water to the reaction mixture, for example about 0.1–29%, preferably 8–15%, or to carry out at a higher temperature without adding water. The amount of the enzyme is preferably from about 2% up to about 50% calculated (w/w) on the substrates. With a 68 hour reaction, a methyl ester of rapeseed oil is completely made to react into products only with an enzyme amount of 10%. The amount of the enzyme needed may be decreased by immobilizing the enzyme. In the process according to the invention, a lipase obtained for example from *Candida rugosa* (ex. *cylindraceae*), *Mucor miehei* or *Pseudomonas fluorescens* may be used. The lipase may also be produced by transforming a gene coding for the desired enzyme into another host organism, by cultivating the host thus obtained and by isolating the lipase produced by it. Commercially obtainable immobilized lipases may be used, or the free lipase may be immobilized before use for example on an ion exchange resin, adsorption resin, celites, diatomaceous earth or silica gel according to the conventional immobilization methods.

The synthetic ester prepared by the process according to the invention is an excellent raw material for the preparation of lubricants. Lubricants, especially hydraulic oils, which contain a synthetic ester prepared by the process of the invention, optionally with one more additives, are also included in the scope of the invention. As additives for example oxidation inhibitors, antiwear agents, antifoam agents, corrosion inhibitors, dispersants, viscosity index improvers and/or pour point depressers which are generally known in the art, may be used.

Oxidation inhibitors include for example amines and phenols. As antiwear agents and corrosion inhibitors for example phosphates or sulfonates and as antifoam agents for example metal sulfonates, metal phenates, polyesters or silicones may be used. Viscosity index improvers include for example polyisobutenes, styrene-butadiene and ethene-propene-copolymers which all are thus suitable also as pour point depressors.

In the following the invention is further described by means of examples, the purpose of which is to illustrate but not to limit the invention.

EXAMPLE 1

A methyl ester of rapeseed oil was prepared as follows: Rapeseed oil (0.3 moles) was weighed into a three-necked flask provided with a thermometer, cooler and a stirring device. Stirring was started and methanol (2.0 moles) was added. The reaction mixture was heated to 60° C. and the alkali catalyst used was added (0.5%, w/w). Stirring was continued for three hours. The progress of the reaction was followed by thin layer chromatography. The reaction mixture was washed with an aqueous acid. The glycerol created in the reaction mixture was separated and the product mixture was analyzed. Rapeseed oil ester content was 97%.

EXAMPLE 2

In a 25 cm$^3$ round bottom flask attached to a Liebig-refluxer of 20 cm with a cold (about +6° C.) tap water circulating in the cooling jacket, was weighed 0.607 g (4.52 mmoles) of solid trimethylol propane (Merck, Darmstadt, Germany), and 0.7 ml of destined water was added. After dissolution, 4.00 g (13.56 mmoles) of methylated rapeseed oil (Raision Yhtymä, Finland) was added and finally 1.79 g of *Candida rugosa* lipase (Biocatalysts Ltd., Pontypridd, Great Britain) in powder form. A negative pressure of 5.3 MPa was sucked into the device. For stirring a magnetic stirrer was attached to the device. The reaction mixture was stirred with the magnetic stirrer at a speed of 200 rpm. The starting point of the reaction was counted from the moment the suction for the reduced pressure was connected to the device. The reaction temperature was 42° C. and the total reaction time 72 hours. The amount of substituted TMP esters in the final product was over 98% in total.

EXAMPLE 3

Example 2 was repeated with 1.84 g of a *Mucor miehei* lipase Lipozyme IM (Novo Nordisk A/S, Bagsvaerd, Denmark) bound to a solid support. Water was not added to the reaction mixture. The reaction temperature was 58° C. The TMPE content of the final product was 75.0% after 24 hours and 92.5% after 66 hours. There were no starting materials left after 66 hours.

EXAMPLE 4

Example 2 was repeated with 1.84 g of a *Candida rugosa* lipase bound to a solid support. 0.7 ml water was added to the reaction mixture. The reaction temperature was 47° C. The TMPE content of the final product was 62.7% after 48 hours and 72.9% after 78 hours.

The enzyme bound to the solid support was prepared as follows: 3.33 g of lipase was dissolved in 100 ml of 0.05M sodium phosphate buffer, stirred for 2 hours and filtrated. To an erlenmeyer flask of 250 ml 40 g of a buffered support (e.g. MWA-1, Mitsubishi Chemical Company, Japan; 43.4% dry matter) and 60 ml of enzyme solution (2 g lipase) was added, shaken for 3 hours at a speed of 130 rpm, filtrated and lyophilized for 30 hours to a dry solids content of 98.9%

EXAMPLE 5

Preparation of a Hydraulic Oil from a Rapeseed Oil Ester and Comparison of Hydraulic Oils The raw material used was the synthetic rapeseed oil ester obtained in Example 2. Said ester was mixed at a certain temperature with additives to obtain a hydraulic oil having the following composition:

| The synthetic ester from Example 2 | 90–98% by weight |
| Oxidation inhibitor | 0.1–2.5% by weight |
| Pour point depresser | 0–5.0% by weight |
| Antiwear agent | 0.1–2.0% by weight |
| Antifoam agent | 0–0.5% by weight |

The technical properties studied of this ester containing additives were wearing, friction, oxidation, low temperature properties and corrosion.

Wear and friction were examined with a four ball test (ASTMD 2783, IP 239) wherein wear with respect to loading or the extreme loading where the lubrication still works, are measured. Oxidative properties were studied with an oxygen bomb test (ASTMD 925) and with the oxidation test DIN 51586 where the change of viscosity at 40° C. was monitored. In a corrosion test (Cincinnati-Milacron test) the aging of the oil as well as copper and steel corrosion were studied. In said test, the change of the total acid number (TAN) and viscosity, the weight change of the copper and steel rods used as oxidation catalysts in the test procedure and the formation of a precipitate under the test conditions are measured. Furthermore, the pour point which illustrates the low temperature properties of an oil was analyzed, i.e. the temperature where the oil is still fluid.

The corresponding properties were examined also from hydraulic oils of the state of the art containing the same additives and from hydraulic oils based directly on rapeseed oil containing also the same additives. The results are shown in Table 1.

TABLE 1

Comparison of the properties of hydraulic oils. A = hydraulic oil with the ester prepared by the process of the invention as raw material, viscosity grade 32; B1 and B2 = hydraulic oils with commercial synthetic esters as raw materials, viscosity grades 46 and 68; C = commercial hydraulic oil based on rapeseed oil, viscosity grade 32.

|  | A | B1 | B2 | C |
|---|---|---|---|---|
| Four ball test | | | | |
| extreme loading, N | 2500 | 3000 | 2500 | 2000 |
| wearing, mm | 0.42 | 0.46 | 0.41 | 0.64 |
| Oxygen bomb test | | | | |
| ASTDM D445, psi | 40 | 39 | 29 | 30 |
| Oxidation inhibition test | | | | |
| DIN 51586, viscosity change, % | 11.5 | 20.3 | 24.1 | 28.8 |
| Cincinnati-Milacron test | | | | |
| TAN mg KOH/g | | | | |
| before | 1.38 | 1.39 | 1.40 | 1.72 |
| after | 1.58 | 3.71 | 2.41 | 0.61 |
| TAN | 0.20 | 2.32 | 1.01 | 1.11 |
| viscosity change, % | 19.0 | 16.9 | 6.2 | 8.2 |
| total precipitate, mg/100 ml | 1.0 | 17.0 | 28.8 | 4.4 |

TABLE 1-continued

Comparison of the properties of hydraulic oils. A = hydraulic oil with the ester prepared by the process of the invention as raw material, viscosity grade 32; B1 and B2 = hydraulic oils with commercial synthetic esters as raw materials, viscosity grades 46 and 68; C = commercial hydraulic oil based on rapeseed oil, viscosity grade 32.

|  | A | B1 | B2 | C |
|---|---|---|---|---|
| weight change of Cu rod, mg | 1.5 | −16.9 | 0 | −0.5 |
| weight change of steel rod, mg | 0.2 | 0.4 | 1.2 | −0.5 |
| Pour point, °C. | −41 | −36 | −39 | −39 |

From the results it can be seen that as regards low temperature properties, the ester prepared by the process according to the invention is equal to the commercial raw materials on the market and better than the commercial product based on rapeseed oil. From the Cincinnati-Milacron test it can be seen that the change of the total acid number (TAN) is clearly the lowest with the ester of the invention. The increase in viscosity at 40° C. is of the same order with all, as well as the weight change of copper and steel rods. The results of the oxygen bomb test are equal, as well as the results of the test according to DIN 51586 and the four ball test.

We claim:

1. An enzymatic process for preparing a synthetic ester from a vegetable oil, comprising
   transesterification of said vegetable oil by reacting it with a lower alkanol to form a mixture of lower alkyl esters of fatty acids,
   a second transesterification reaction wherein the obtained mixture of esters is reacted in the presence of a lipase triacylglycerol acylhydrolase; EC 3.1.1.3, with a no beta hydrogen polyol of the formula

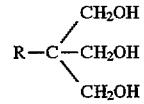

wherein R is a $C_1$–$C_6$ alkyl group or a —$CH_2OH$ group, and recovering the synthetic ester obtained.

2. The process according to claim 1, wherein the vegetable oil is rapeseed oil.

3. The process according to claim 1, wherein the lower alkanol is a $C_1$–$C_4$ alkanol.

4. The process according to claim 1, wherein the fatty acid lower alkyl ester is a methyl ester of a fatty acid.

5. The process according to claim 1, wherein the no beta hydrogen polyol is selected from the group consisting of trimethylol ethane, trimethylol propane, trimethylol butane and pentaerythritol.

6. The process according to claim 1, wherein the second transesterification reaction is carried out in the presence of an immobilized lipase.

7. The process according to claim 1, wherein the second transesterification reaction is carried out in the presence of a *Candida rugosa* lipase.

8. The process according to claim 1, wherein the second transesterification reaction is carried out in the presence of a *Mucor miehei* lipase.

9. The process according to claim 1, wherein the lipase is separated after the reaction and recycled.

10. The process according to claim 1, wherein the second transesterification reaction is carried out with a lipase obtained by transforming a gene coding for said enzyme into another host organism for producing the lipase.

11. The process according to claim 1, wherein the reaction mixture contains about 0.1 to 29% water.

12. The process according to claim 1, wherein the reaction temperature in the second transesterification is between 37° C. and 69° C.

13. The process according to claim 1, wherein the no beta hydrogen polyol and the mixture of esters are reacted with each other in a molar ratio of from about 1:2 to 1:6.

14. A lubricant composition comprising a synthetic ester obtained according to claim 1, optionally with one or more additives.

15. The lubricant composition according to claim 14 which comprises about 90 to 98% of a synthetic ester and about 2 to 10% of additives.

16. The lubricant composition according to claim 14 wherein the additive is selected from the group consisting of an oxidation inhibitor, an antiwear agent, an antifoam agent, a corrosion inhibitor, a dispersant, a viscosity index improver, a pour point depresser and mixtures thereof.

17. The process according to claim 2, wherein the second transesterification reaction is carried out in the presence of an immobilized lipase.

18. The process according to claim 3, wherein the second transesterification reaction is carried out in the presence of an immobilized lipase.

19. The process according to claim 4, wherein the second transesterification reaction is carried out in the presence of an immobilized lipase.

20. The process according to claim 1, wherein the lower alkanol is methanol or ethanol.

\* \* \* \* \*